United States Patent [19]
Negus et al.

[11] Patent Number: 5,893,848
[45] Date of Patent: Apr. 13, 1999

[54] GAUGING SYSTEM FOR MONITORING CHANNEL DEPTH IN PERCUTANEOUS ENDOCARDIAL REVASCULARIZATION

[75] Inventors: Charles Christopher Negus; Stephen J. Linhares, both of Taunton; Robert L. Rudko, Holliston; Eileen A. Woodruff, Millis, all of Mass.

[73] Assignee: PLC Medical Systems, Inc., Franklin, Mass.

[21] Appl. No.: 08/735,658

[22] Filed: Oct. 24, 1996

[51] Int. Cl.$^6$ ............................................. A61B 5/05
[52] U.S. Cl. .................. 606/41; 606/10; 606/31; 606/1; 607/122
[58] Field of Search .................. 606/1, 10–17, 606/27–32, 38–42, 45–50; 607/100–102, 122; 604/21, 22

[56] References Cited

U.S. PATENT DOCUMENTS

| | | | |
|---|---|---|---|
| 5,083,573 | 1/1992 | Arms | 600/587 |
| 5,391,199 | 2/1995 | Ben-Haim | 607/122 |
| 5,423,809 | 6/1995 | Klicek | 606/38 |
| 5,425,367 | 6/1995 | Shapiro et al. | 600/11 |
| 5,599,347 | 2/1997 | Hart et al. | 606/42 |
| 5,643,253 | 7/1997 | Baxter et al. | 606/17 |

Primary Examiner—Michael Peffley
Attorney, Agent, or Firm—Iandiorio & Teska

[57] ABSTRACT

A gauging system for monitoring channel depth in percutaneous endocardial revascularization surgery includes a catheter for percutaneous insertion into a heart chamber, including a source of tissue ablative energy for ablating a part of the wall of the heart chamber where a channel is to be created; a sensor device proximate the distal end of the catheter for sensing a boundary of the heart wall proximate the channel; and a detection circuit, responsive to the sensor device, for determining the position of the terminus of the channel in the heart chamber; alternatively, a mechanical stop extending radially beyond the distal tip may be used for physically limiting penetration of the catheter tip into the drilled channels.

18 Claims, 10 Drawing Sheets

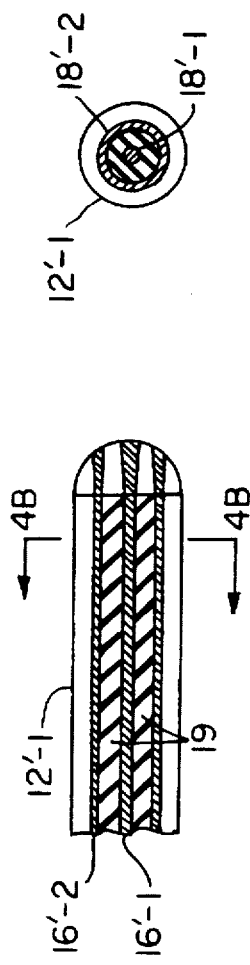
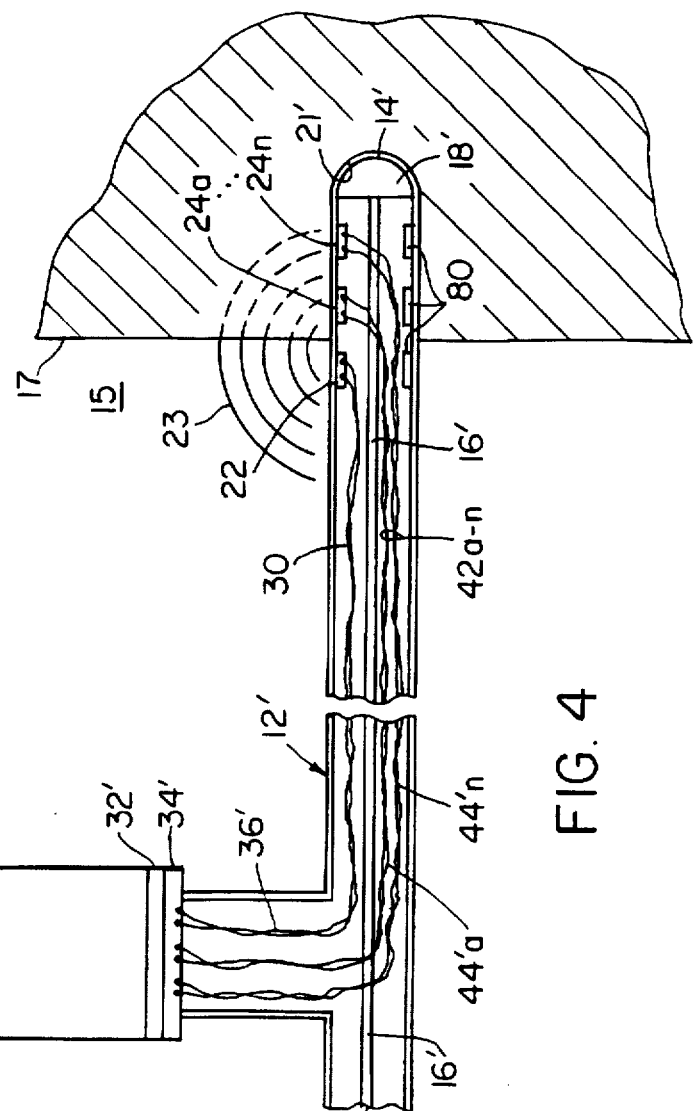
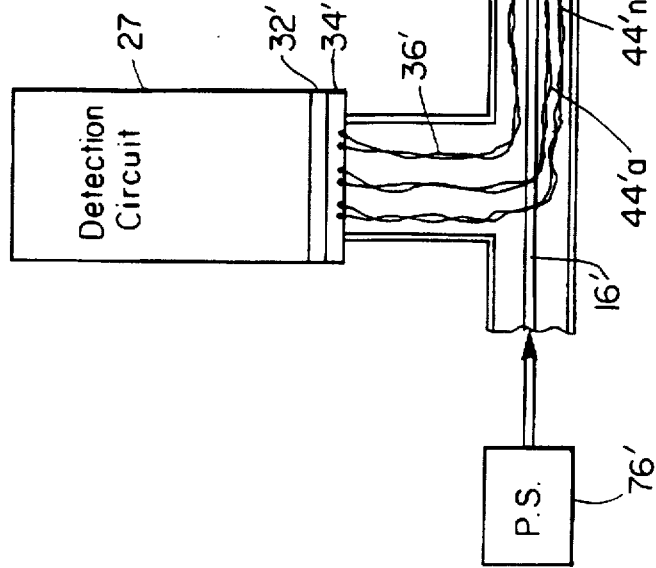

GAUGING SYSTEM FOR MONITORING CHANNEL DEPTH IN PERCUTANEOUS ENDOCARDIAL REVASCULARIZATION

FIELD OF INVENTION

This invention relates to an improved gauging system for monitoring channel depth in percutaneous endocardial revascularization surgery.

BACKGROUND OF INVENTION

Transmyocardial revascularization (TMR), including endocardial revascularization (ECR), is a surgical treatment for cardiovascular disease. Present ECR procedure is an open chest technique which uses a laser beam to drill holes in the myocardium, specifically a chamber of the heart, typically the left ventricle. These holes or channels extend through the entire heart wall thickness from the outside through to the ventricle. The channels heal on the outside surface of the heart due to external pressure from the surgeon, but remain open on the inside, allowing blood to enter the heart wall tissue from the ventricle.

In another approach ECR could be performed percutaneously using a catheter introduced percutaneously so that the tip of the catheter is inside a chamber of the heart, typically the left ventricle, where the holes or channels can be created from the inside toward but not through the outside of the heart. The energy used to drill these channels can be mechanical, e.g., a needle; electrical, e.g., bipolar or unipolar electric current, r.f., microwave; or optical, e.g., laser. In one combined optical and mechanical approach a holmium laser initiates the channel and a force is applied through the tip of the catheter to deepen the channel. Typically a holmium (HO:YAG) laser or an excimer laser would be used percutaneously. One problem in percutaneous ECR is that, unlike in open chest TMR, channels being drilled are not plainly visible but their depth must be controlled to prevent the channel going all the way through the myocardium and penetrating the outer wall of the heart. Monitoring of the depth can be done with biplanar fluoroscopy but this is expensive and can be confusing even to experienced physicians under the stress of performing heart surgery. This approach is not very reliable; is expensive; requires additional equipment in the operating theater. In another approach the cumulative amount of energy consumed during a drilling is monitored and the drilling is stopped when a certain amount of energy has been expended. This assumes a correlation between hole depth and applied ablative energy and also assumes a thickness of the heart wall, both of which are approximations at best and cannot be relied on for accurate depth gauging. This is a particularly serious problem that needs accurate gauging because if the channel punches through the outer wall of the heart the patient could bleed to death or die of cardiac tamponade if the pericardium is not open due to previous surgery, for example. That would require emergency action to open the chest and stanch the bleeding. This technique, using delivered energy to estimate channel depth, is not reliably accurate nor consistent.

SUMMARY OF INVENTION

It is therefore an object of this invention to provide a gauging system for monitoring channel depth in percutaneous endocardial revascularization surgery.

It is a further object of this invention to provide such a gauging system which is reliable, inexpensive, requires virtually no additional equipment or space and is easy to interpret.

It is a further object of this invention to provide such a gauging system which is accurate and consistent.

The invention results from the realization that a truly safe, reliable and inexpensive gauging system for monitoring channel depth in percutaneous endocardial revascularization surgery which does not require extensive equipment or special expertise can be effected with a catheter that delivers ablative energy to the area of the heart wall to be drilled and a sensor device including at least one sensor element proximate the distal tip of the catheter for sensing the depth of the channel or of the remaining heart wall.

This invention features a gauging system for monitoring channel depth in percutaneous endocardial revascularization surgery including a catheter for percutaneous insertion into a heart chamber, including a source of tissue ablative energy for ablating a part of the wall of the heart chamber where a channel is to be created. A sensor device proximate the distal end of the catheter senses a boundary of the heart wall proximate the channel and a detection circuit, responsive to the sensor device, determines the position of the terminus of the channel in the heart chamber.

In a preferred embodiment the energy source may be at the proximal end of the catheter and may include a conduit for conveying the ablative energy to and out of the distal end of the catheter. The energy source may be a laser. The conduit may include a fiber optic element in which the conduit includes an electrical power supply at the proximal end of the catheter and electrical conductor means extending through the catheter. The energy source may include an ultrasonic transducer at the distal end of the catheter interconnected with the electrical conductor means. The energy source may include an electrode at the distal end of the catheter interconnected with the electrical conductor means. The energy source may include two opposite polarity electrodes at the distal end of the catheter interconnected with the electrical conductor means. The sensor device may include a sensor for sensing the ablative energy reflected from the heart chamber wall. The sensor device may include a transmitter element for emitting sensing energy and a sensor element for sensing the reflection of that sensing energy from the heart chamber wall. The sensor device may include sensor means for sensing a difference in a property between the heart chamber wall and the blood in the chamber. The detection circuit may include means for determining the depth of the channel created in the heart chamber wall. The detection circuit may include means for determining the remaining thickness of the heart chamber wall beyond the channel created in the heart chamber wall. The sensor element may be a capacitive device and the physical property sensed may be the force exerted on the tip. The sensor element may be a resistive device and the physical property sensed may be the force exerted on the tip. The sensor element may be a piezoelectric device and the physical property sensed may be the force exerted on the tip. The source of ablative energy may be interrupted, redirected, or turned off when a predetermined channel depth has been reached.

The invention also features a gauging system for monitoring channel depth in percutaneous endocardial revascularization surgery including a catheter for percutaneous insertion into a heart chamber including a source of tissue ablative energy for ablating a part of the wall of the heart chamber where a channel is to be created and a mechanical stop extending radially beyond the distal tip for physically limiting penetration of the catheter tip into the drilled channels. In a preferred embodiment the mechanical stop may be longitudinally movable along the catheter to adjust the penetration limit of the tip. The mechanical stop may include a sensor device including at least one sensor element for sensing the difference in a physical property between the heart tissue and the blood in the chamber.

The invention also features a gauging system for monitoring channel depth in percutaneous endocardial revascularization surgery including a catheter for percutaneous insertion into a heart chamber including a source of tissue ablative energy for ablating a part of the heart wall where a channel is to be created. A sensor device includes a transmitter for transmitting a signal for propagation through at least one of the heart tissue and blood and a sensing element proximate the distal end of the catheter for sensing the signal from the transmitter. A detection circuit, responsive to the sensor device, determines the position of the terminus of the channel in the heart chamber.

In a preferred embodiment the signal may be an optical signal or it may be an acoustic signal.

This invention also features a gauging system for monitoring channel depth in percutaneous endocardial revascularization surgery including a catheter for percutaneous insertion into a heart chamber including a source of tissue ablative energy for ablating a part of the heart wall where a channel is to be created. A sensor device including at least one sensor element proximate the distal end of the catheter senses the difference in force exerted on the sensor element by the heart tissue and the blood and a detection circuit responsive to the sensor device determines the position of the terminus in the channel in the heart chamber.

In a preferred embodiment the sensor element may be a resistive device or a capacitive device or a piezoelectric device.

DISCLOSURE OF PREFERRED EMBODIMENT

Other objects, features and advantages will occur to those skilled in the art from the following description of a preferred embodiment and the accompanying drawings, in which:

FIG. 4 is a schematic diagram of an alternative construction of the catheter tip according to this invention;

FIG. 4A is a side sectional view of a bipolar tip according to this invention;

FIG. 4B is a sectional view taken along line 4B—4B of FIG. 4A;

Figure 1:
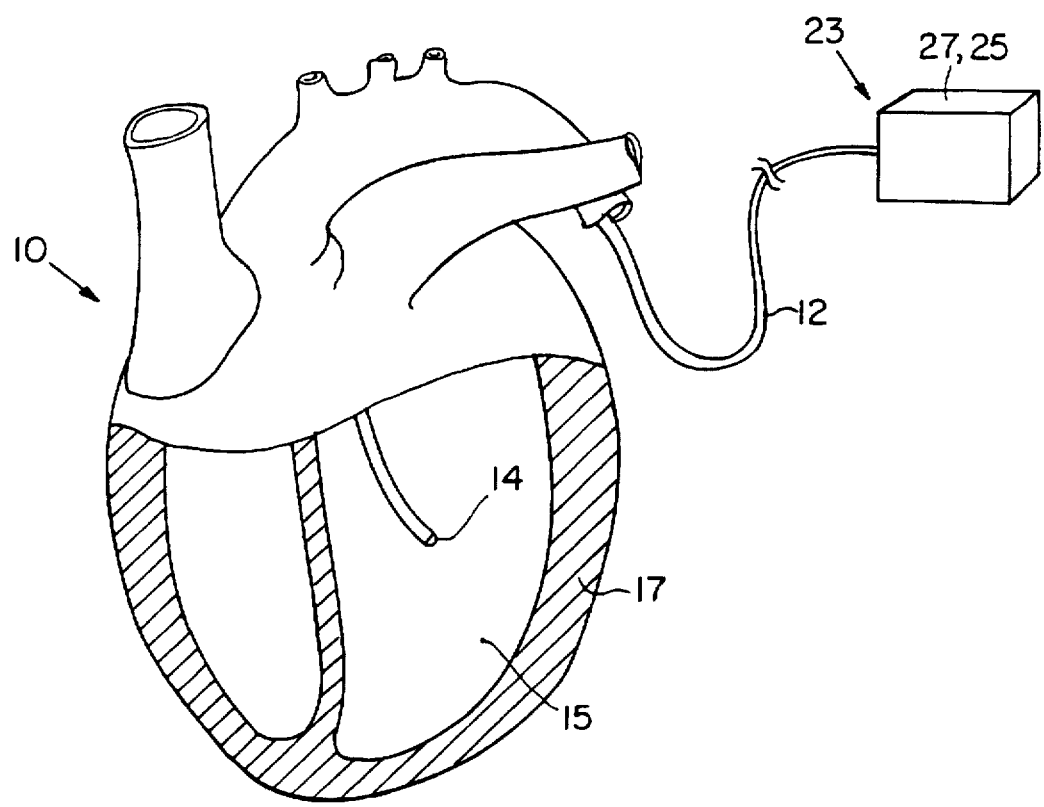
FIG. 1 is a three-dimensional partially sectioned view of a human heart showing a catheter with its tip disposed in a chamber of the heart, typically the left ventricle.
Figure 2:
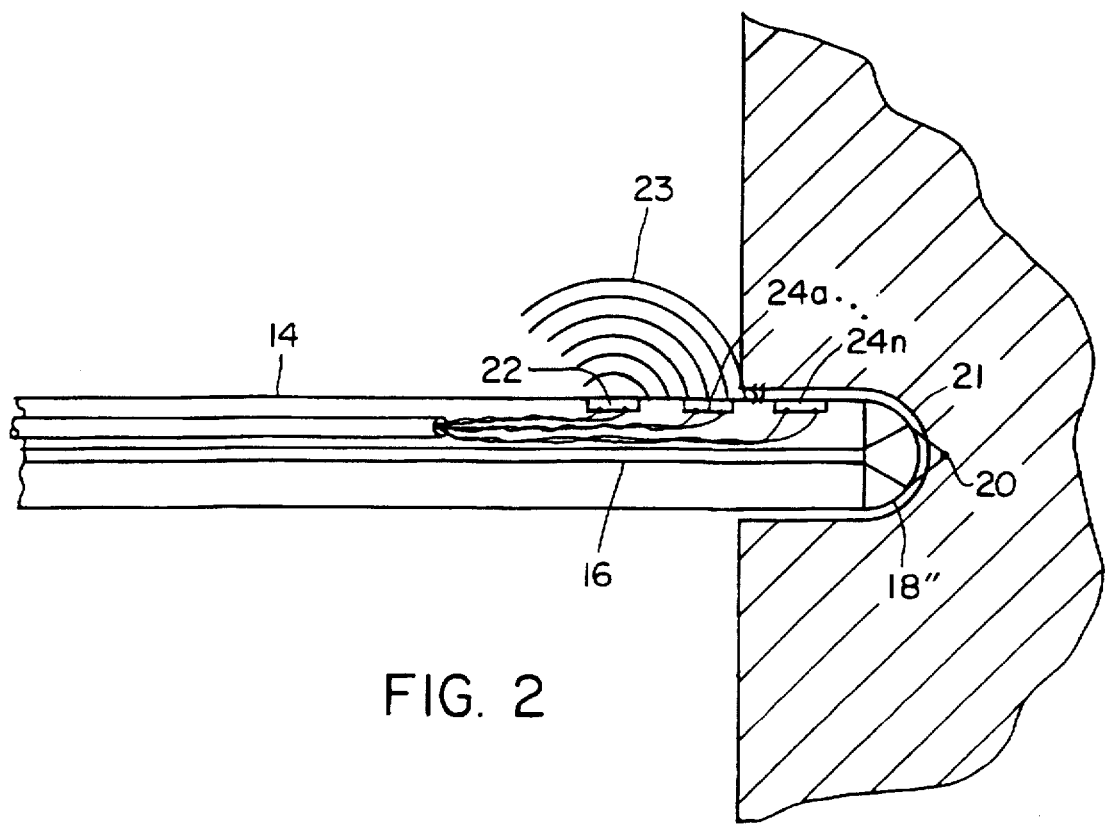
FIG. 2 is an enlarged detailed view of the tip of the catheter of FIG. 1.

There is shown in FIG. 1 a human heart 10 having a catheter 12 according to this invention inserted through the aorta with tip 14 at its distal end disposed in a chamber of the heart, typically the left ventricle, immersed in the blood 15 and approaching the wall 17 of the left ventricle. A housing at the proximal end of catheter 12 includes an ablative energy source 25 and detector circuit 27. An enlarged detail view of tip 14, FIG. 2, shows that it includes a conduit 16 for delivering energy to, e.g., electrodes, to an acoustic transducer, or optical lens. In the structure of FIG. 2 optical lens 18 focuses the energy at a point 20 to ablate tissue in the heart wall and create a channel 21. Distal tip 14 includes a sensing device including transmitter 22 which may be an acoustic or optical transmitter that sends out a signal or radiation 23 which passes through the blood in the ventricle and is received by one or more sensor elements 24a–24n which would be acoustic or optical sensors, respectively. The radiation 23, be it optical or acoustic, is chosen so that it is attenuated more by one of the blood and heart tissue. Thus as tip 14 using the energy from lens 18 creates a channel 21 in the heart wall, the change in the signal sensed by the series of sensor elements 24a–24n gives an indication of just how deep the tip has penetrated into the heart wall. The greater the number and the closer the spacing of sensor elements 24a–24n, the higher will be the resolution of the penetration.

Figure 3:
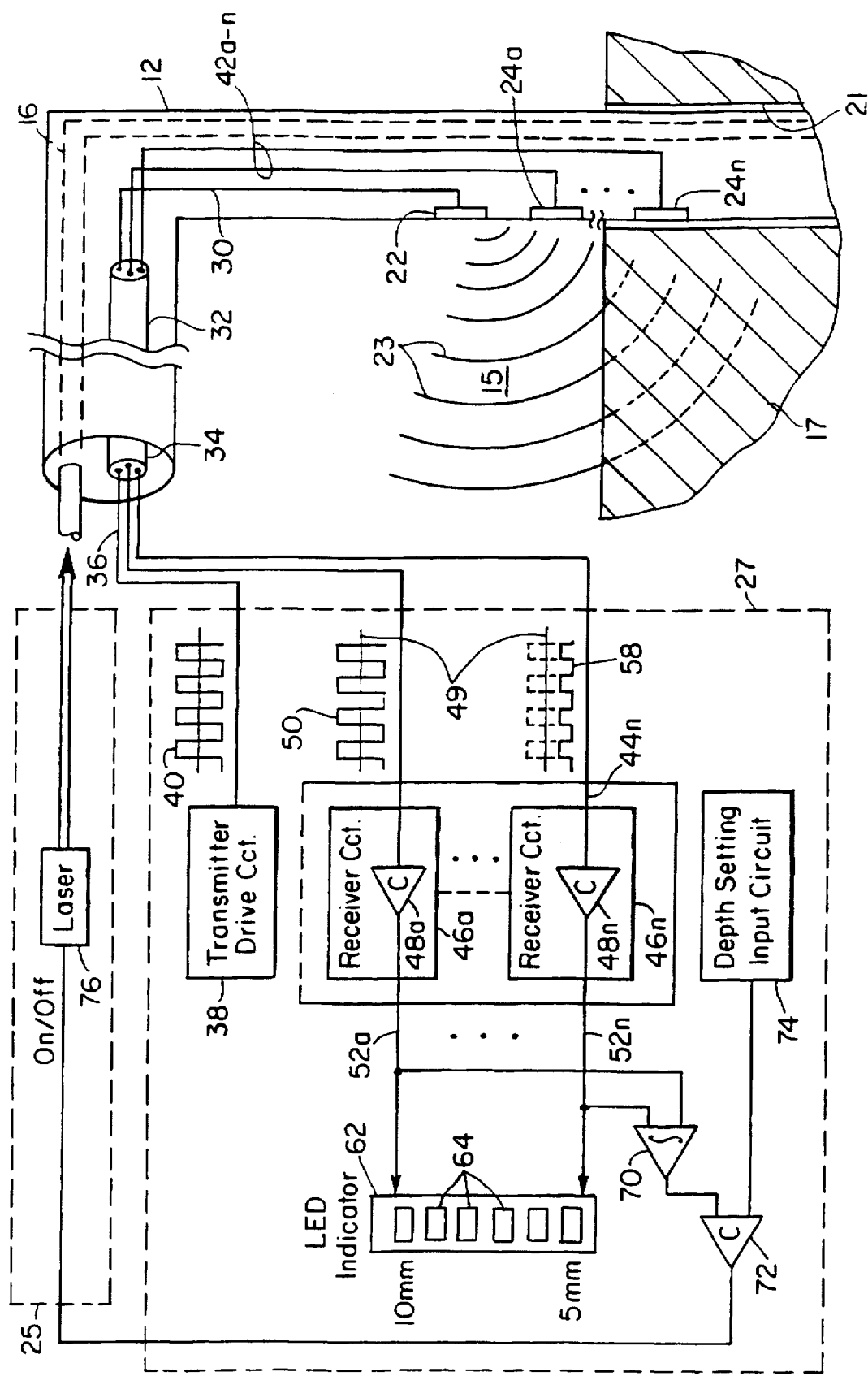
FIG. 3 is a schematic diagram of the catheter and a detection circuit according to this invention.

Transmitter 22, FIG. 3, is connected through wire 30, connectors 32 and 34, and wire 36 to detection circuit 27 including transmitter drive circuit 38 which provides a signal that is a series of output pulses 40 to transmitter 22. Sensor elements 24a–n are connected through wires 42a–n, connectors 32 and 34 and wires 44a–n to their respective receiver circuits 46a–n. A comparator 48a–n in each of the receiver circuits 46a–n thresholds the incoming signal at a predetermined level 49, assuming for example that the radiation signal 23 put out by transmitter 22 is attenuated more by tissue 17 than by blood 15. For when the return signal is above threshold 49 the system understands that the particular sensor delivering that signal is still exposed to the blood in the ventricle where a sensor element returning a signal below that threshold is accepted as being proximate the tissue in the drilled channel. Thus sensor element 24a provides a signal which is well above threshold 49 indicating that it is still immersed in the blood 15. Thus receiver circuit 46a puts out a signal on line 52a indicating it is seeing blood. Sensor element 24n, being partway down the drilled passage 21 in heart wall 17, receives an attenuated version of the output signal 40 from transmitter 22 so its return signal 58 is below threshold 49 and comparator 48n in receiver circuit 46n thus puts out a signal on line 52n indicating tissue is being seen by sensor element 24n. An indicator such as LED indicator 62 may be driven by receivers 46a–n so that as more and more of the sensor elements 24a–n become exposed to the tissue, more and more LED indicator elements 64 are energized. The six LED indicator elements in LED indicator 62 may for example indicate a depth of penetration of 5 mm to 10 mm typically.

Although in this specific example the tissue is referred to as the greater attenuator of the signal, this is not a necessary limitation of the invention as the blood could be the greater attenuator or one of them could be a complete blocker while the other one propagates well or passably well. The outputs 52a–n of receiver circuits 46a–n are also delivered to integrator 70 which integrates the signals from all of the receivers 46a–n and provides that cumulative output to comparator 72 where it is compared with a predetermined depth setting from depth setting input circuit 74. When the integrated value of all of the outputs of receiver circuits 46a–n exceeds the predetermined depth setting from circuit 74, comparator 72 provides the signal to laser 76 so that it stops introducing energy into conduit 16 which in this case may be a fiber optic element. Alternatively, laser 76 could be replaced by an electrical energy source which would energize an acoustic transducer at the distal end.

In an alternative construction, catheter 12', FIG. 4, may have for its conduit an electric conductor wire 16' which is energized by an electrical power supply 76' instead of a laser. Wire 16' connects with at least one electrode 18'. With a single electrode, a unipolar system is formed; with two electrodes a bipolar system would be formed. A bipolar system is shown in FIGS. 4A and 4B where conduit 16' includes a central conductor 16'-1 and coaxial conductor 16'-2 which terminate in electrodes 18'-1, 18'-2, with suitable insulation 19. One or more additional sensor elements 80 may be used in addition to sensor elements 24a–n.

Figure 5:
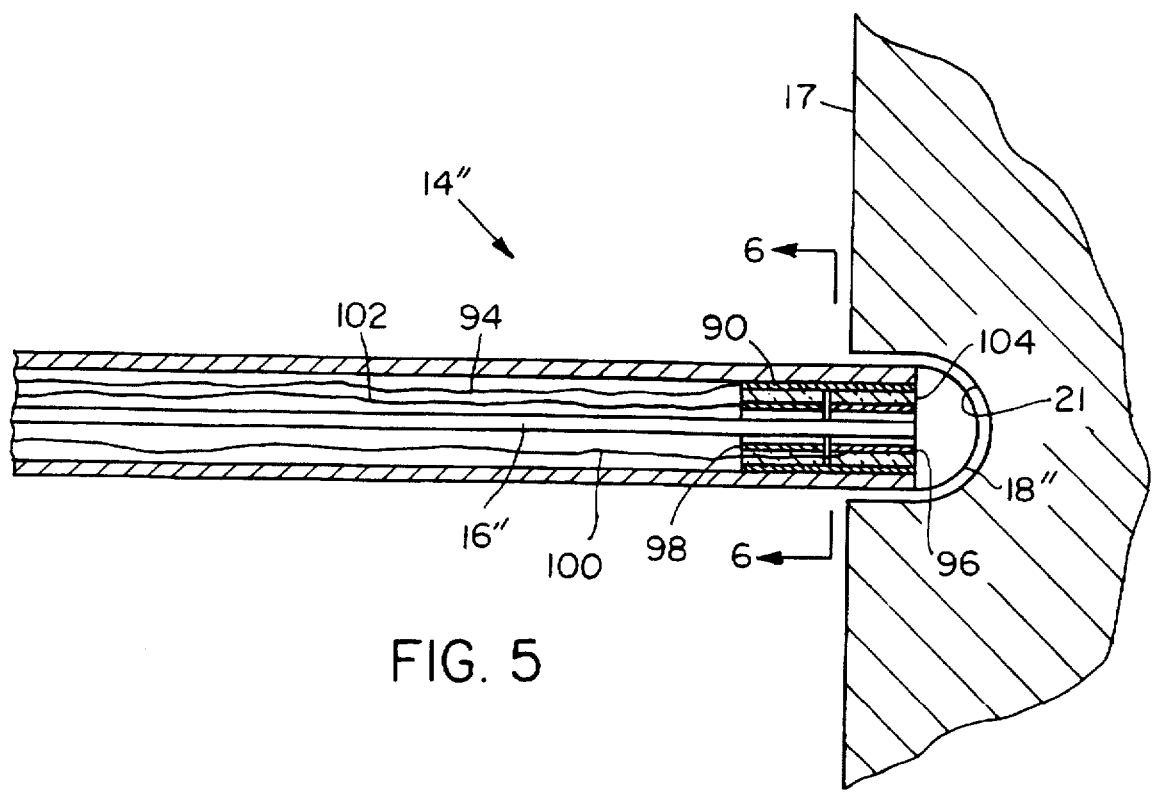
FIG. 5 is an enlarged detailed sectional view similar to FIG. 2 of an alternative construction of the catheter tip according to this invention.
Figure 6:
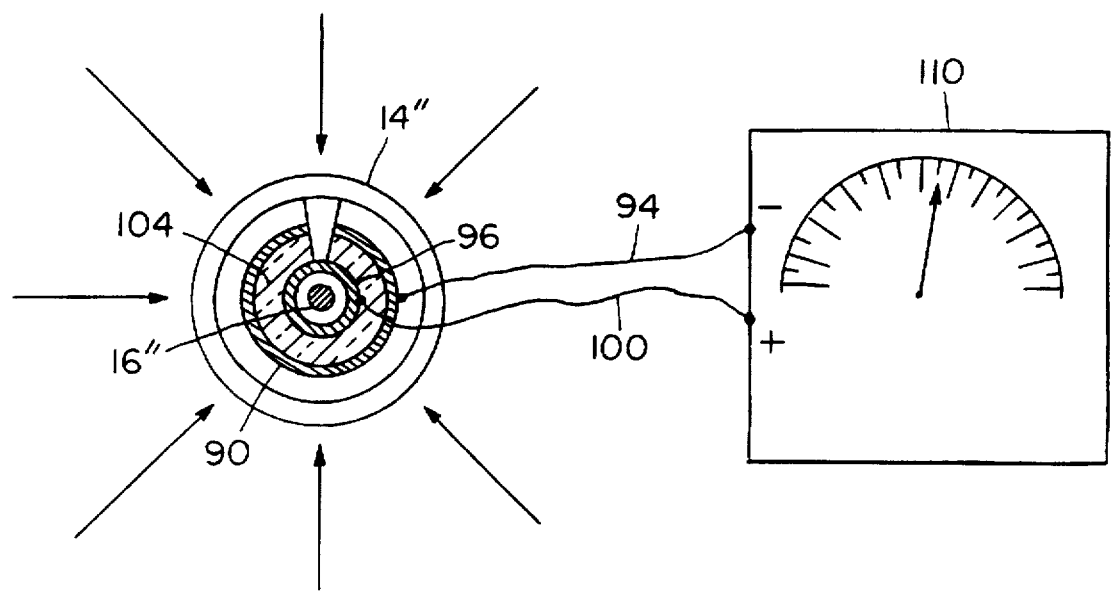
FIG. 6 is a sectional view taken along line 6—6 of FIG. 5 showing an illustrative impedance or voltage meter for reading the effects of the external force on the tip of FIG. 5.
Figure 7:
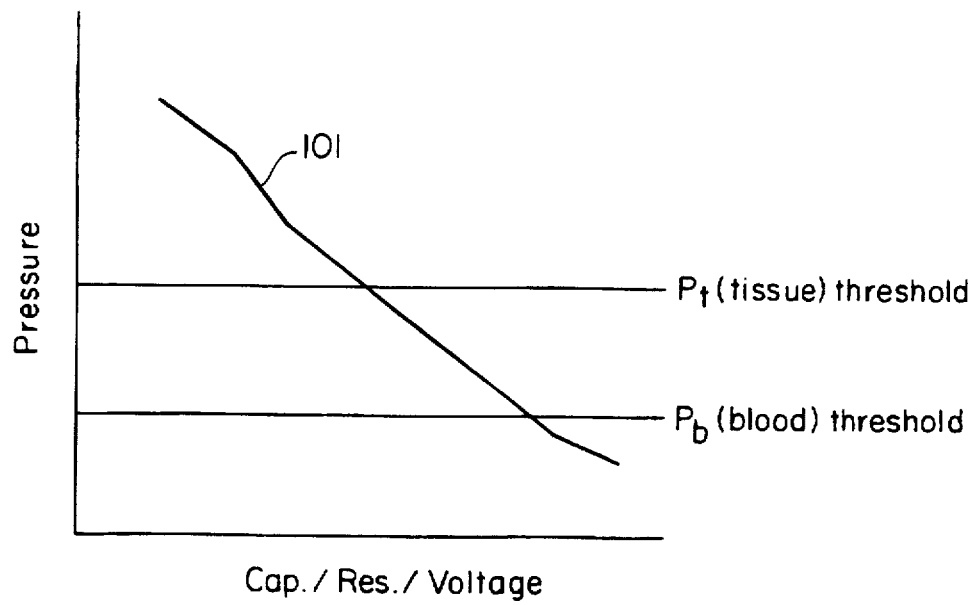
FIG. 7 shows a characteristic change in capacitance, resistance or voltage with the change in pressure exerted on the tip of FIGS. 5 and 6.

In another construction, tip 14", FIG. 5, may use resistive, capacitive or piezoelectric material (by piezoelectric material is meant ferroelectric and magnetostrictive as well as conventional piezoelectric material) or a force sensing coupling to determine the force exerted on the tip. The difference in force applied to the tip by the blood and the heart tissue can be detected as an indication of the depth of penetration of tip 14" into the heart wall. In this construction there may be a common circumferential electrode 90 interconnected with the detection circuit by wire 94 and two separate additional electrodes 96, 98 interconnected with the detection circuit by wires 100 and 102, respectively. The annular medium 104 between those electrodes may be a resistive material whose resistance changes under the influence of pressure or it may be a dielectric material so that the electrodes in the dielectric material act as a capacitance whose capacitance will change under the influence of the pressure, or medium 104 may be a piezoelectric material whose voltage output will vary in accordance with the pressure exerted upon it. Whichever of those implementations is chosen, the output from the electrodes, for example electrodes 90 and 96, may be delivered over wires 94 and 100, FIG. 6, to a detection device, illustratively indicated as meter 110, which indicates the level of capacitance, resistance or voltage sensed. Depending upon that level, the calibrated pressure commensurate with that particular capacitance, resistance or voltage can be determined as can be seen from the characteristic pressure curve 101 in FIG. 7. Then a determination can be made as to whether the particular sensor is seeing tissue or blood. For example, if the threshold $P_t$ is exceeded then that particular sensor is looking at tissue. If only the threshold $P_b$ is exceeded then it is determined that that sensor element is still seeing the blood.

Figure 8:
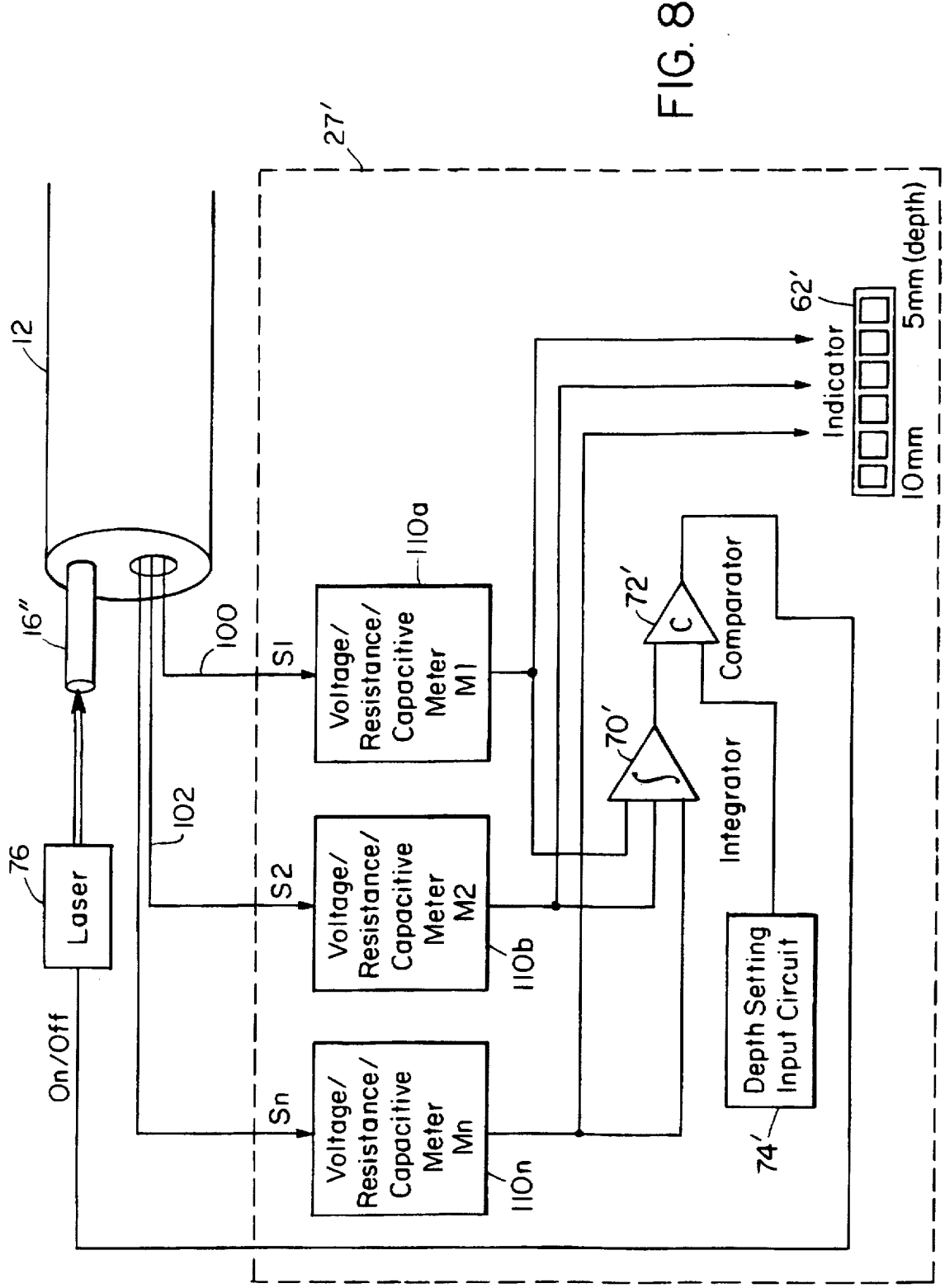
FIG. 8 is a schematic diagram of a detection circuit for use with the tip of FIG. 5.

In a typical implementation, the sensing device will include a number of sensor elements so there will be a number of voltage/resistance/capacitance meters 110a–110n, FIG. 8, whose outputs will be delivered to integrator 70' and indicator 62' as explained previously with respect to FIG. 3. The operation of integrator 70' with comparator 72' and depth setting input circuit 74' in FIG. 8 is also similar to their operation in FIG. 3.

Figure 9:
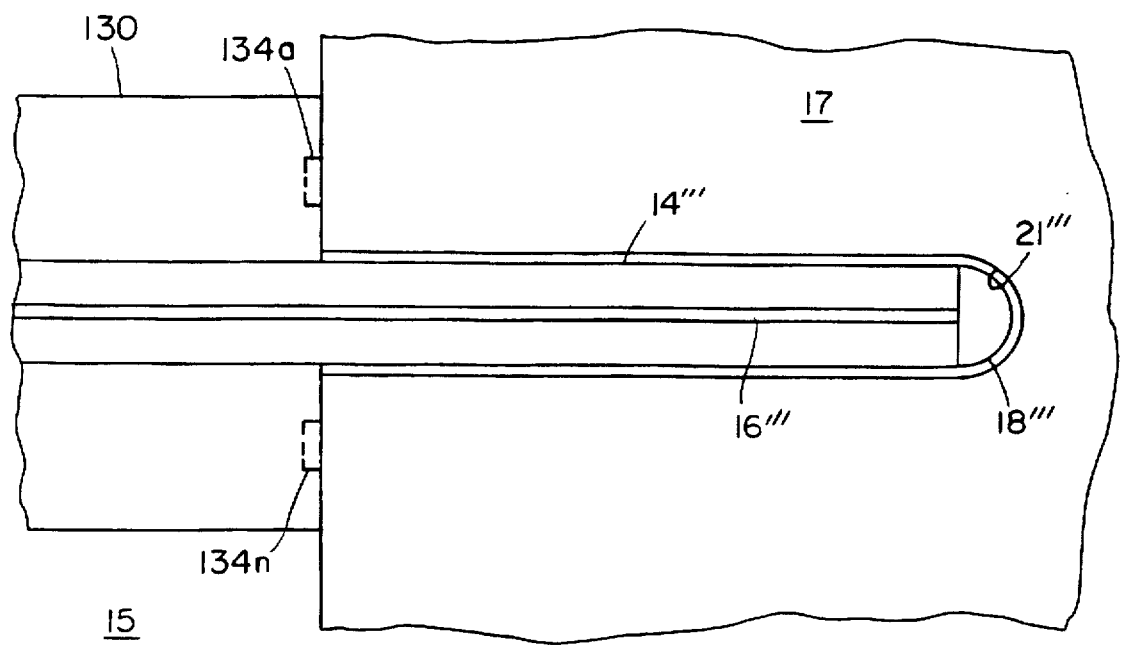
FIG. 9 is a schematic diagram of the distal tip of a catheter including a mechanical stop according to this invention.
Figure 10:
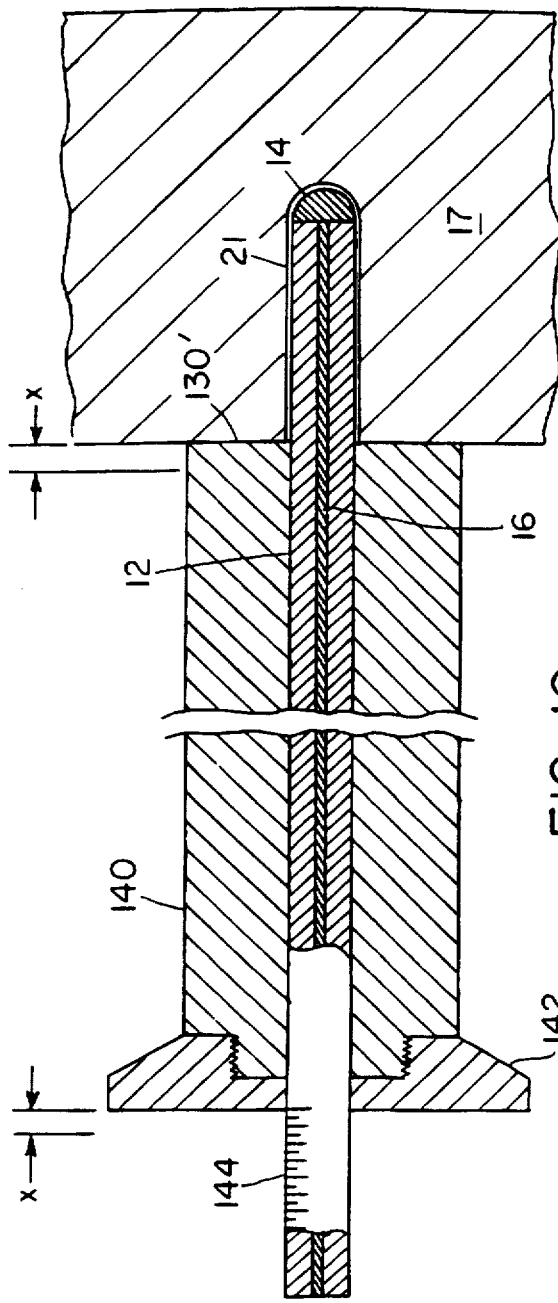
FIG. 10 is a schematic sectional diagram of a mechanical stop similar to that shown in FIG. 9 which is adjustable.

A mechanical stop 130, FIG. 9, can be provided so that tip 14'" can only penetrate so far into heart wall 17 as limited by stop 130 which extends radially outwardly from tip 14'". Mechanical stop 130 may also be provided with one or more sensor elements 134a–n which for example sense the increased pressure exerted on them by the heart wall 17 as opposed to that exerted by blood 15 as an indication that the desired penetration limit has been reached. The limit set by stop 130 can be made adjustable by providing a stop catheter 140, FIG. 10, which fits over catheter 12 and carries on its forward end stop 130'. A locking knob or jam nut 142 is loosened to slide stop catheter 140 forward or back on catheter 12 to set the desired position of mechanical stop 130'. Then locking knob or jam nut 142 is tightened down to secure stop catheter 140 in that position on catheter 12. Ruled gauging lines 144 may be provided so that the limiting distance chosen can be easily determined.

Although thus far the ablation and gauging functions are shown as operating independently, that is not a limitation of the invention. For example, where the ablation energy is propagatable, e.g., optical, ultrasonic, the ablation energy 150, FIG. 11, may be sensed by sensor 152 as it is reflected 154 from a boundary of the heart wall 17, e.g., the boundary of the blood and heart wall at the terminus 156 of channel 21, or from the boundary 158 of the heart wall 17 and the surrounding fluid 160 to determine the position of the terminus 156 of the channel relative to the inner surface 157 (depth of channel) or the outer surface 159 (wall thickness remaining). Additionally, when ultrasonic energy is used the ultrasonic transducer 162, FIG. 12, which emits the ablative ultrasonic energy 164 can be used to sense the reflected ultrasonic energy 166 from the same heart wall boundaries to locate the terminus of the channel.

Figure 12:
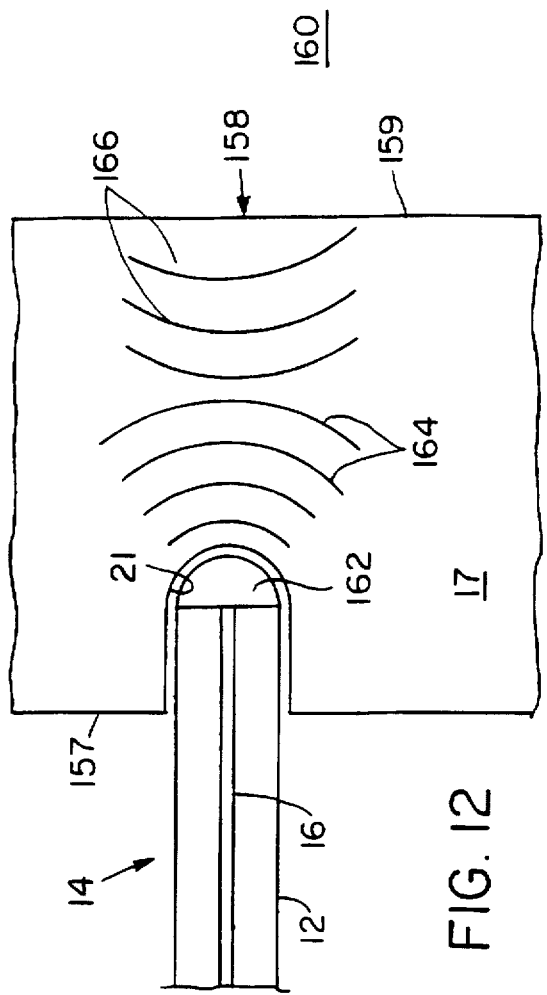
FIG. 12 is a schematic diagram of an ultrasonic ablative catheter tip which uses the ultrasonic ablative energy to sense the channel penetration.
Figure 11:
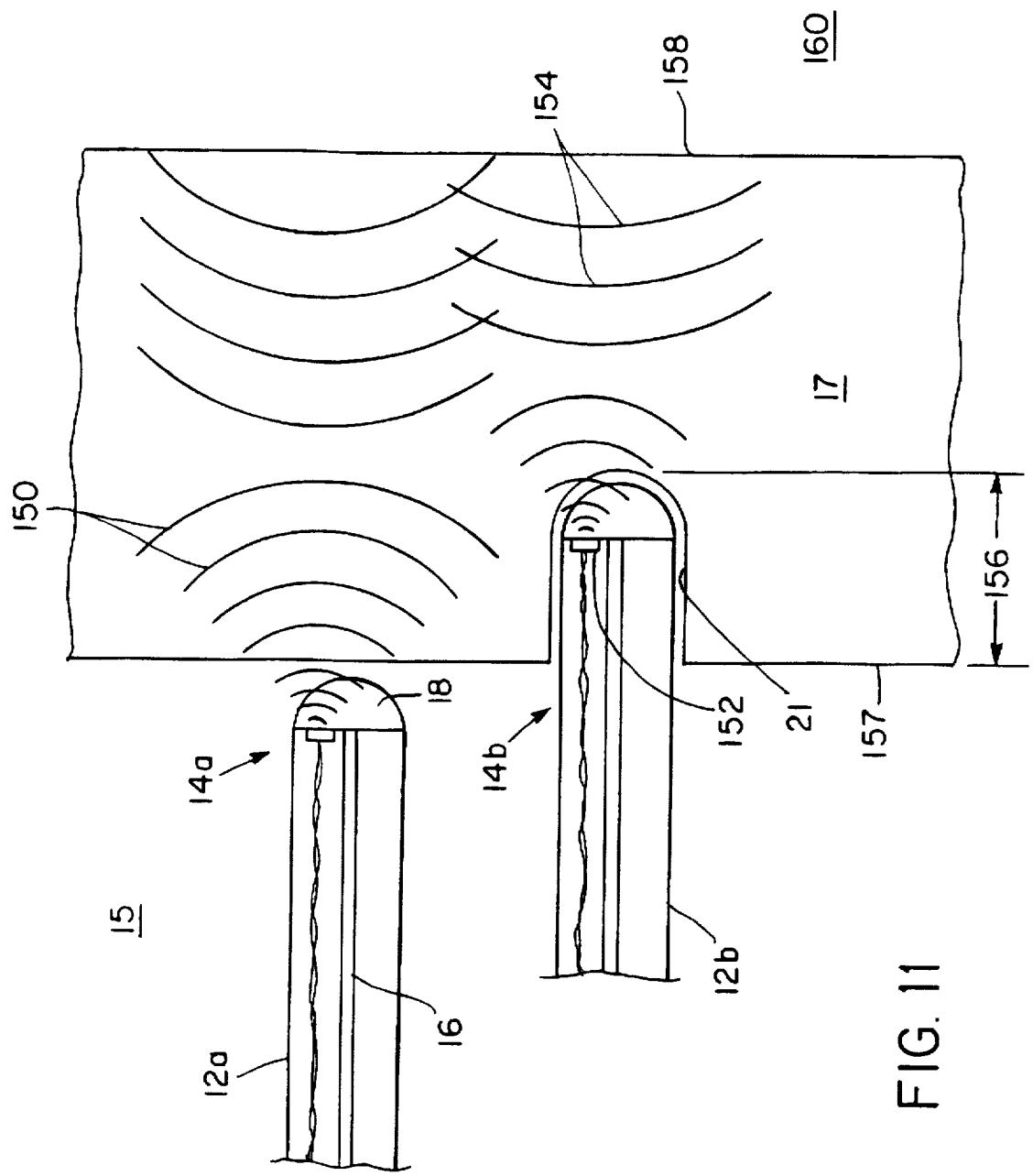
FIG. 11 is a schematic diagram showing sequential movement of an ultrasonic ablative catheter tip with a separate ultrasonic system for sensing the channel penetration.
Figure 13:
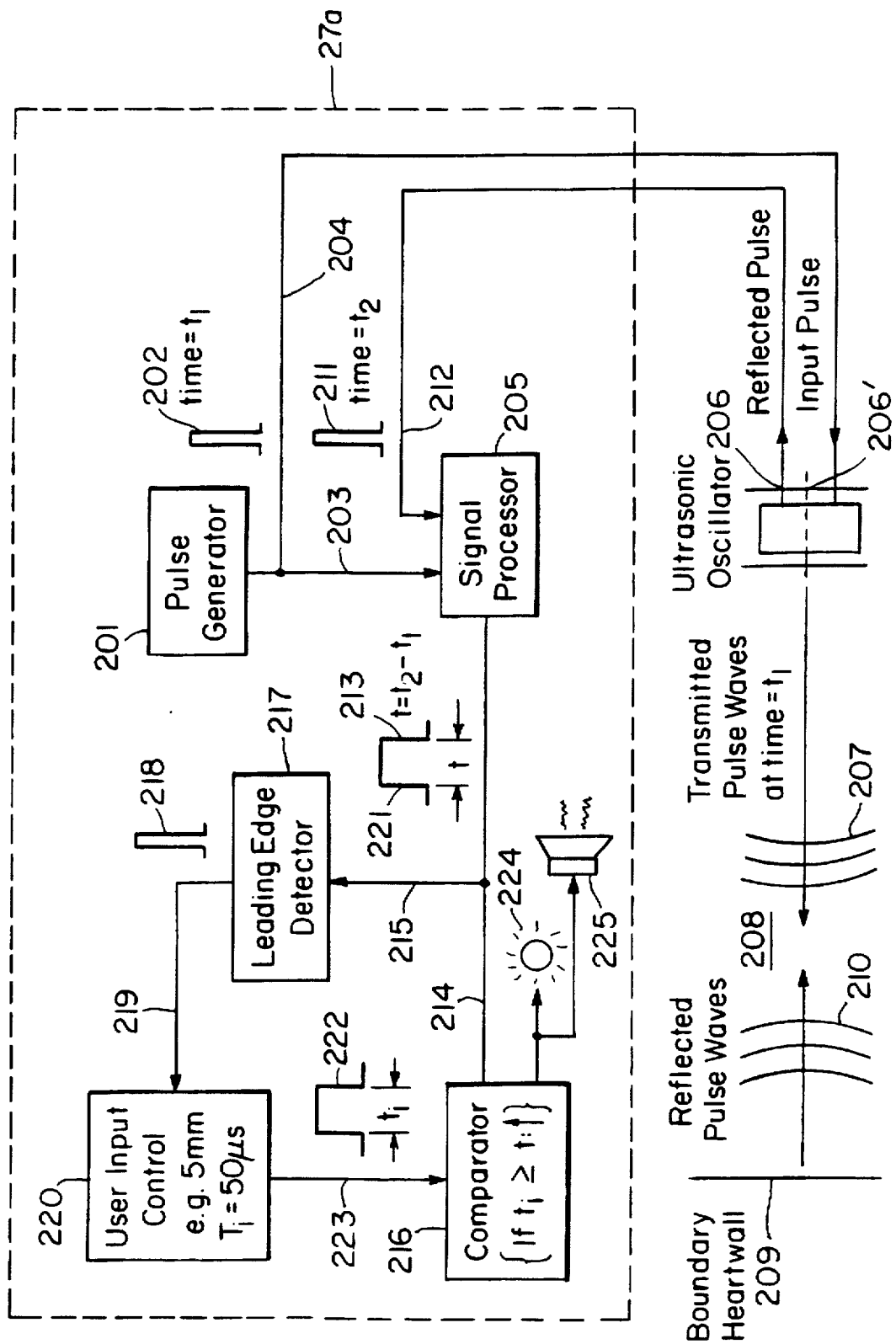
FIG. 13 is a more detailed schematic diagram of a detection circuit usable with the tip of FIG. 11.
Figure 14:
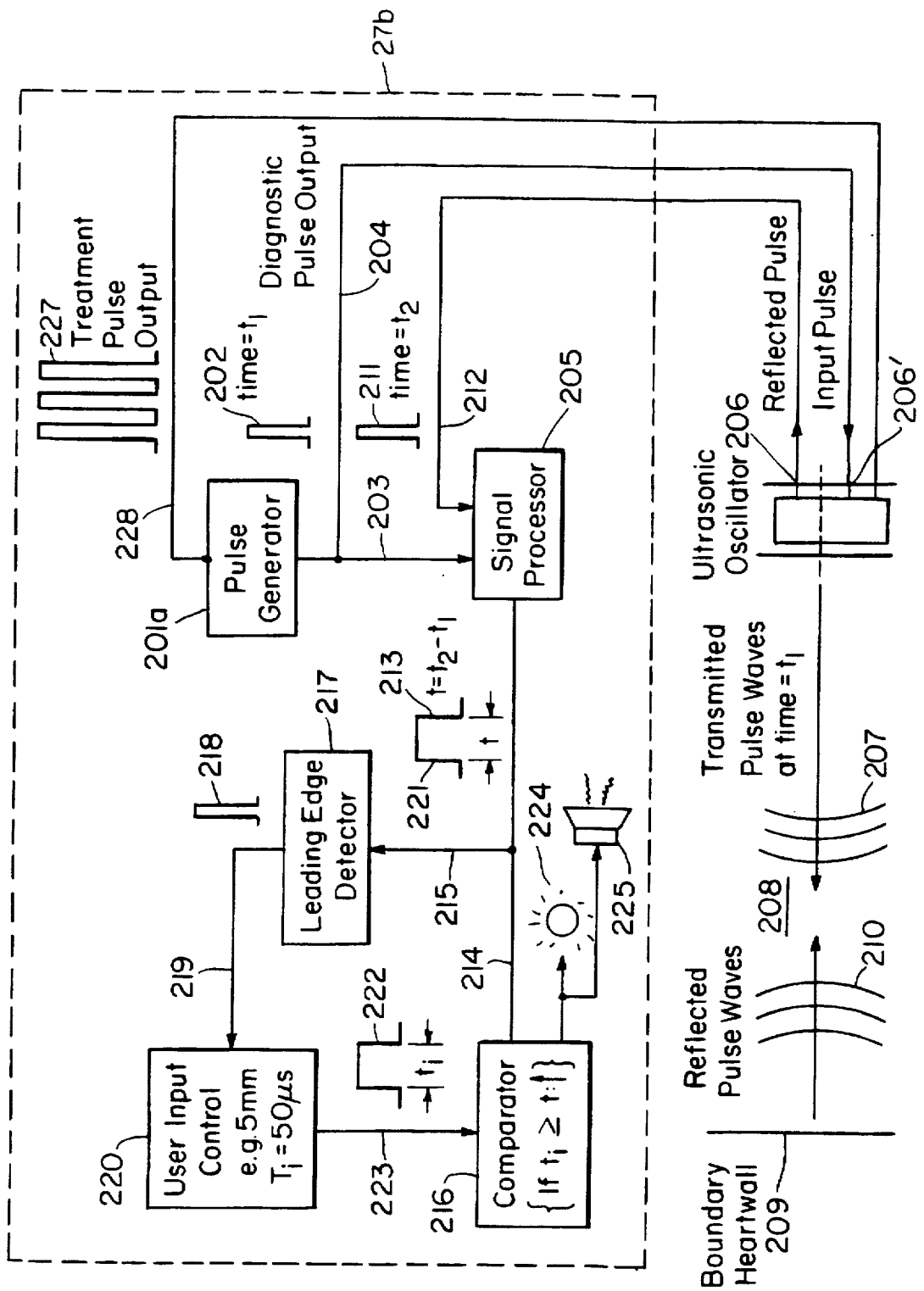
FIG. 14 is a more detailed schematic diagram of a detection circuit usable with the tip of FIG. 12.

Detection circuits associated with the apparatus of FIGS. 11 and 12 are shown in FIGS. 13 and 14, respectively. In detection circuit 27a, FIG. 13, pulse generator 201 emits pulse 202, at a time, $t_1$, along lines 203 and 204 to signal processor 205, and ultrasonic detector 206, respectively. Ultrasonic detector 206 then emits an ultrasonic wave 207, which is transmitted through tissue 208, and is reflected from tissue boundary 209. The reflected waves 210 are absorbed by ultrasonic detector 206, or 206', if a separate detector is used, as denoted by the dotted line through it. The absorbed waves generate a pulse 211, at time $t_2$, which is then sent to the signal processor over line 212. The signal processor compares the time difference t between the first input pulse 202, and the responding pulse 211, and emits a waveform 213, corresponding to the round-trip time for the waves to travel to the boundary and back to the detector. Waveform 213 travels along lines 214 and 215 to a comparator 216 and a leading edge detector 217, respectively. Leading edge detector generates a pulse 218 which is emitted over line 219 as soon as the leading edge 221 of waveform 213 is seen by leading edge detector 217. Pulse 218 enables user input control 220 to emit a preselected waveform 222 over line 223 to comparator 216. Waveform 222 is chosen to correspond to a given length of time $t_i$ for ultrasonic waves to travel a set distance (i.e., 5 mm) in tissue and reflect back from a boundary to its origin. The comparator 216 then compares t to $t_i$ and when $t_i \geq t$ turns on an indicator lamp 224 and/or buzzer 225 to indicate that the preselected depth has been reached. Pulse 202 may be at a frequency and/or amplitude to also ablate tissue to create a channel, and the transmitted waves 207 may be the residual from that ablation.

FIG. 14 is identical except that pulse generator 201a also generates treatment pulses over line 228 to ultrasonic detector 206 for ablating tissue to create a channel. The pulses 227 may be at a different frequency, amplitude, and/or phase than pulse 202, FIG. 13.

Although the channel 21' in FIG. 4 is shown only as deep as the penetration of tip 14', this is not a necessary limitation of the invention, for as shown in FIG. 9 the channel 21'" may and typically does extend beyond the tip 14'"5.

Other embodiments will occur to those skilled in the art and are within the following claims:

What is claimed is:

1. A gauging system for monitoring channel depth in percutaneous endocardial revascularization surgery, comprising:

a catheter for percutaneous insertion into a heart chamber, including a source of tissue ablative energy for ablating a part of a wall of the heart chamber where a channel is to be created;

a sensor device proximate a distal end of said catheter for sensing a boundary of the heart wall proximate the channel; and a detection circuit, responsive to said sensor device, for determining a position of a terminus of said channel.

2. A gauging system for monitoring channel depth in percutaneous endocardial revascularization surgery of claim 1 in which said source of tissue ablative energy is at a proximal end of said catheter and includes a conduit for conveying the ablative energy to and out the distal end of said catheter.

3. The gauging system for monitoring channel depth in percutaneous endocardial revascularization surgery of claim 2 in which said source of tissue ablative energy is a laser.

4. The gauging system for monitoring channel depth in percutaneous endocardial revascularization surgery of claim 3 in which said conduit includes a fiber optic element.

5. The gauging system for monitoring channel depth in percutaneous endocardial revascularization surgery of claim 2 in which said conduit includes an electrical power supply at the proximal end of said catheter and electrical conductor means extending through the catheter.

6. The gauging system for monitoring channel depth in percutaneous endocardial revascularization surgery of claim 5 in which said source of tissue ablative energy includes an ultrasonic transducer at the distal end of said catheter interconnected with said electrical conductor means.

7. The gauging system for monitoring channel depth in percutaneous endocardial revascularization surgery of claim 5 in which said source of tissue ablative energy includes an electrode at the distal end of said catheter interconnected with said electrical conductor means.

8. The gauging system for monitoring channel depth in percutaneous endocardial revascularization surgery of claim 1 in which said sensor device includes sensor means for sensing a difference in a physical property between the heart chamber wall and the blood in the chamber.

9. The gauging system for monitoring channel depth in percutaneous endocardial revascularization surgery of claim 8 in which said sensor element is a capacitive device and the physical property sensed is the force exerted on the tip.

10. The gauging system for monitoring channel depth in percutaneous endocardial revascularization surgery of claim 8 in which said sensor element is a resistive device and the physical property sensed is the force exerted on the tip.

11. The gauging system for monitoring channel depth in percutaneous endocardial revascularization surgery of claim 8 in which said sensor element is a piezoelectric device and the physical property sensed is the force exerted on the tip.

12. A gauging system for monitoring channel depth in percutaneous endocardial revascularization surgery, comprising:

a catheter for percutaneous insertion into a heart chamber, for ablating a part of a wall of the heart chamber where a channel is to be created;

a mechanical stop extending radially from a distal tip of the catheter for physically limiting penetration of the distal tip into the channels; and at least one sensor element on the mechanical stop for detecting when the mechanical stop is in contact with the wall of the heart chamber.

13. The gauging system for monitoring channel depth in percutaneous endocardial revascularization surgery of claim 12 in which said at least one sensor element senses the difference in a physical property between the heart tissue and blood in the chamber.

14. A gauging system for monitoring channel depth in percutaneous endocardial revascularization surgery, comprising:

a catheter, for percutaneous insertion into a heart chamber, for ablating a part of the heart wall where a channel is to be created;

a sensor device including at least one sensor element proximate a distal end of said catheter for sensing the difference in force exerted on said sensor element by the heart tissue and the blood; and a detection circuit, responsive to said sensor device, for determining the position of a terminus of the channel in said heart chamber.

15. The gauging system for monitoring channel depth in percutaneous endocardial revascularization surgery of claim 14 in which said sensor element is a resistive device.

16. The gauging system for monitoring channel depth in percutaneous endocardial revascularization surgery of claim 14 in which said sensor element is a capacitive device.

17. The gauging system for monitoring channel depth in percutaneous endocardial revascularization surgery of claim 14 in which said sensor element is a piezoelectric device.

18. The gauging system for monitoring channel depth in percutaneous endocardial revascularization surgery of claim 14 in which said detection circuit includes means for ceasing emission of tissue ablative energy when a predetermined depth has been reached.

* * * * *